US008683865B2

(12) United States Patent
Steinhoff et al.

(10) Patent No.: US 8,683,865 B2
(45) Date of Patent: Apr. 1, 2014

(54) ULTRASONIC SCANNING WITH LOCAL GAIN INTERVALS (75) Inventors: Norbert Ewald Steinhoff, Erftstadt (DE); Alexander Franz Freund, Pulheim (DE); Markus Manfred Stahlberg, Bornheim (DE)

(73) Assignee: General Electric Company, Schenectady, NY (US)

( * ) Notice: Subject to any disclaimer, the term of this patent is extended or adjusted under 35 U.S.C. 154(b) by 347 days.

(21) Appl. No.: 13/116,887

(22) Filed: May 26, 2011

(65) Prior Publication Data

US 2012/0297881 A1    Nov. 29, 2012

(51) Int. Cl.
*G01N 29/00* (2006.01)

(52) U.S. Cl.
USPC .................. 73/605; 73/626; 73/631

(58) Field of Classification Search
USPC .................... 73/606, 626, 631, 629
See application file for complete search history.

(56) References Cited

U.S. PATENT DOCUMENTS

| 4,205,555 A | * | 6/1980 | Hashiguchi ............. 73/626 |
| 5,150,714 A | * | 9/1992 | Green .................. 600/442 |
| 5,507,184 A | | 4/1996 | Freund et al. |
| 5,555,180 A | | 9/1996 | Hilger et al. |
| 5,841,889 A | * | 11/1998 | Seyed-Bolorforosh ....... 382/128 |
| 5,891,038 A | * | 4/1999 | Seyed-Bolorforosh et al. ............. 600/447 |
| 6,705,996 B2 | * | 3/2004 | Kawagishi et al. ........... 600/458 |
| 6,973,831 B2 | * | 12/2005 | Satoh ................. 73/618 |

FOREIGN PATENT DOCUMENTS

GB    2279523    1/1995

* cited by examiner

*Primary Examiner* — J M Saint Surin
(74) *Attorney, Agent, or Firm* — Hiscock & Barclay LLP (57) ABSTRACT

A device is disclosed that, in an illustrative embodiment, includes an input line, a main gain component, a first local gain component, and a second local gain component. The main gain component, the first local gain component, and the second local gain component each have a communicative connection with the input line. The main gain component is configured for applying a main gain to an ultrasonic wave signal received via the input line, thereby providing a main gain signal. The first local gain component is configured for applying a first local gain to a portion of the ultrasonic wave signal within a first signal gate, and thereby providing a first local gain signal. The second local gain component is configured for applying a second local gain to a portion of the ultrasonic wave signal within a second signal gate, and thereby providing a second local gain signal.

20 Claims, 4 Drawing Sheets

ULTRASONIC SCANNING WITH LOCAL GAIN INTERVALS

BACKGROUND OF THE INVENTION

The invention disclosed herein relates to the field of nondestructive testing, and in particular to nondestructive testing using ultrasonic scanning.

Nondestructive testing devices can be used to inspect test objects to identify and analyze flaws and defects in the objects both during and after an inspection. In one type of nondestructive testing, an operator maneuvers a probe at or near the surface of the test object in order to perform testing of both the object surface and underlying structure. Nondestructive testing can be particularly useful in some industries, e.g., aerospace, power generation, and oil and gas recovery and refining, where object testing must take place without removal of the object from surrounding structures, and where hidden defects can be located that would otherwise not be identifiable through visual inspection, particularly where finished components are costly to make and are desired to go into commercial use. Nondestructive testing may also be useful for measuring the thickness of a test subject.

One example of nondestructive testing is ultrasonic testing. When conducting ultrasonic testing, an ultrasonic pulse can be emitted from a probe and passed through a test object at the characteristic sound velocity of that particular material. The sound velocity of a given material depends in part on the modulus of elasticity, temperature and density of the material. Application of an ultrasonic pulse to a test object causes an interaction between the ultrasonic pulse and the test object structure, with sound waves being reflected back to the probe. The corresponding evaluation of the signals received by the probe, namely the amplitude and time of flight of those signals, can allow conclusions to be drawn as to the internal quality of the test object without destroying it. In particular, the ultrasonic pulse will reflect off of and refract through any internal discontinuities in the test object, such as material abnormalities. Such irregular reflections and refractions not caused by the known external boundaries of the test object may be taken as indications of damage or abnormality in the test object. The timing of the returning signals from such irregular reflections and/or refractions may be analyzed to indicate the position and size of such damage or abnormality within the test object.

Generally, an ultrasonic testing system includes a probe for sending and receiving signals to and from a test object, a probe cable connecting the probe to an ultrasonic test unit, and a screen or monitor for viewing test results. The ultrasonic test unit can include power supply components, signal generation, amplification and processing electronics, and device controls used to operate the nondestructive testing device. Some ultrasonic test units can be connected to computers that control system operations, as well as test results processing and display. Electric pulses can be generated by a transmitter and can be fed to the probe where they can be transformed into ultrasonic pulses by ultrasonic transducers.

Ultrasonic transducers may incorporate piezoelectric ceramics which can be electrically connected to a pulsing-receiving unit in the form of an ultrasonic test unit. Portions of the surfaces of the piezoelectric ceramics can be metal coated, forming electrodes that can be connected to the ultrasonic test unit. During operation, an electrical waveform pulse may be applied to the electrodes of the piezoelectric ceramic, causing a mechanical change in ceramic dimension and generating an acoustic wave that can be transmitted through a material such as a metal or plastic to which the ultrasonic transducer is coupled. Conversely, when an acoustic wave reflected from the material under inspection contacts the surface of the piezoelectric ceramic, it generates a voltage difference across the electrodes that is detected as a receive signal by the ultrasonic test unit or other signal processing electronics.

The amplitude, timing and transmit sequence of the electrical waveform pulses applied by the pulsing unit can be determined by various control means incorporated into the ultrasonic test unit. The pulse is generally in the frequency range of about 0.5 MHz to about 25 MHz, so it is referred to as an ultrasonic wave from which the equipment derives its name. As the ultrasonic pulses pass through the object, various pulse reflections called echoes occur as the pulse interacts with any internal structures, voids, or other abnormalities within the test object and with the opposite side (back surface) of the test object. The echo signals can be displayed on the screen with echo amplitudes appearing as vertical traces and time of flight or distance as horizontal traces. By tracking the time difference between the transmission of the electrical pulse and the receipt of the electrical signal and measuring the amplitude of the received wave, various characteristics of the material can be determined. Thus, for example, ultrasonic testing can be used to determine material thickness or the presence and size of imperfections within a given test object.

The discussion above is merely provided for general background information and is not intended to be used as an aid in determining the scope of the claimed subject matter.

BRIEF DESCRIPTION OF THE INVENTION

Systems, methods, and devices are disclosed for performing ultrasonic scanning with local gains applied to portions of an ultrasonic wave signal, in accordance with a variety of illustrative embodiments. One illustrative advantage that may be realized in the practice of some disclosed embodiments is to ensure that abnormalities deeper within a test subject are identified within a higher gain scanning signal, to compensate for an otherwise weaker scanning signal due to greater signal attenuation by greater diffusion, interference, and noise relative to defects with a more shallow position within a test subject. This may help ensure that all defects within a test subject are equally likely to be detected by an ultrasonic scanning operator, regardless of depth within the test subject.

In one illustrative embodiment, a device is disclosed. In an illustrative embodiment, the device includes an input line, a main gain component, a first local gain component, and a second local gain component. The main gain component, the first local gain component, and the second local gain component each have a communicative connection with the input line. The main gain component is configured for applying a main gain to an ultrasonic wave signal received via the input line, thereby providing a main gain signal. The first local gain component is configured for applying a first local gain to a portion of the ultrasonic wave signal within a first signal gate, and thereby providing a first local gain signal. The second local gain component is configured for applying a second local gain to a portion of the ultrasonic wave signal within a second signal gate, and thereby providing a second local gain signal.

In another illustrative embodiment, an ultrasonic scanning system is disclosed. The ultrasonic scanning system may include an ultrasonic wave transducer, a processing component, an output component, and a monitor. The ultrasonic wave transducer may be configured for transmitting and receiving ultrasonic waves, and generating an ultrasonic wave signal based on reflected ultrasonic waves it receives. The ultrasonic wave signal generated by the ultrasonic wave transducer may therefore take the form of an electrical signal generated as a function of or based on the reflected ultrasonic waves it receives. The ultrasonic wave signal is an ultrasonic wave signal in the sense that it is a signal based on the reflected ultrasonic waves as detected by the ultrasonic wave transducer. The processing component may have a communicative connection with the ultrasonic wave receiver and may be configured to receive the ultrasonic wave signal and to apply a main gain to the ultrasonic wave signal to provide a main gain signal, to apply a first local gain to a portion of the ultrasonic wave signal within a first signal gate to provide a first local gain signal, and to apply a second local gain to a portion of the ultrasonic wave signal within a second signal gate to provide a second local gain signal. The output component may output the main gain signal, the first local gain signal, and the second local gain signal. The monitor may have a communicative connection with the output component.

In another illustrative embodiment, a method for scanning a test subject with an ultrasonic wave is disclosed. The method includes transmitting an ultrasonic wave through a test subject. The method further includes receiving a reflected ultrasonic wave from the test subject. The method further includes generating an ultrasonic signal based on the reflected ultrasonic wave. The method further includes applying a main gain to the ultrasonic signal. The method further includes applying a first local gain to a first portion of the ultrasonic signal corresponding to a first portion of the test subject. The method further includes applying a second local gain to a second portion of the ultrasonic signal corresponding to a second portion of the test subject. The method further includes displaying a graph on a monitor of the ultrasonic signal with the main gain applied to it, the first portion of the ultrasonic signal with the first local gain applied to it, and the second portion of the ultrasonic signal with the first local gain applied to it.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
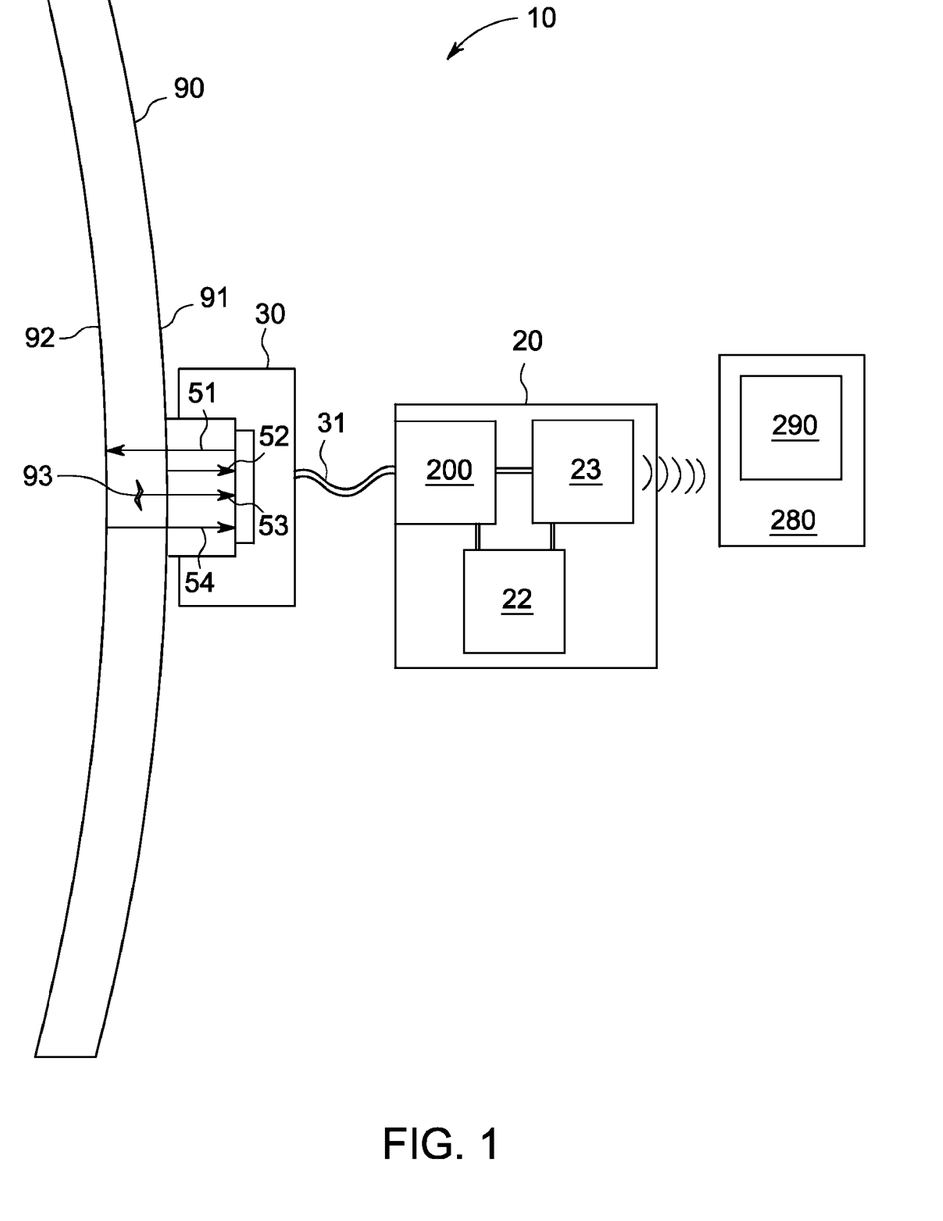
FIG. 1 depicts a schematic block diagram for an ultrasonic scanning system for providing signal graphs showing ultrasonic signals with a main gain and/or local gains versus depth in a test subject, in accordance with an illustrative embodiment.

FIG. 1 depicts a schematic block diagram for an ultrasonic scanning system 10 for providing signal graphs showing ultrasonic RF signals with a main gain and/or local gains versus depth in a test subject 90, in accordance with an illustrative embodiment. Various aspects of this illustrative embodiment are described as follows, with the understanding that many other embodiments use different variations and aspects. Ultrasonic scanning system 10 includes ultrasonic control device 20 and ultrasonic wave transducer 30, connected to ultrasonic control device 20 with cable 31 that provides a communicative connection between the two elements.

In this illustrative embodiment, ultrasonic control device 20 includes processing component 200, power supply component 22, and output component 23. Output component 23 may have a communicative connection with processing component 200, such as with a system bus, for example, and power supply component 22 may be operatively connected to processing component 200 and output component 23. Processing component 200 has a communicative connection with ultrasonic wave transducer 30 through cable 31. Output component 23 may be a wireless transmitter or transceiver of some type, for example, and may transmit output signals to computing device 280 having monitor 290, in this illustrative example. In other embodiments, ultrasonic control device 20 may have a monitor of its own and display output signals on its own monitor, for example, and may have other components such as a memory component, which it may use for buffering data before transmitting it, for example.

In other embodiments, an ultrasonic scanning system may have variations such as additional or fewer components, or different arrangements or methods for providing an output to a monitor, for example.

Ultrasonic wave transducer 30 may include both an ultrasonic wave transmitter and an ultrasonic wave receiver (not individually labeled in the figure). The ultrasonic wave transmitter and the ultrasonic wave receiver may therefore both be included in the ultrasonic wave transducer 30. The ultrasonic wave transmitter may be configured to receive commands from ultrasonic control device 20 and to transmit ultrasonic frequency sound waves, while the ultrasonic wave receiver may be configured to receive ultrasonic frequency sound waves, translate them into an ultrasonic signal, and provide the ultrasonic signal to processing component 200. The ultrasonic signal thus provided may be in the form of an electrical signal, for example, which may be received and processed by processing component 200, as described further below.

As seen in a simplified schematic form in FIG. 1, ultrasonic wave transducer 30 may transmit an ultrasonic wave 51 into test subject 90. One component of ultrasonic wave 51 may reflect off the forward surface 91 of test subject 90, as reflected ultrasonic wave 52. Another component of ultrasonic wave 51 may reflect off the back surface 92 of test subject 90, as reflected ultrasonic wave 54. Both of these wave reflections are expected, from the expected form of test subject 90. The thickness of the test subject 90 may, for example, be evaluated as one-half the difference in time between the ultrasonic wave transducer 30 receiving the reflected ultrasonic wave 52 from the forward surface 91 and receiving the reflected ultrasonic wave 54 from the back surface 92, times the speed of sound within the test subject 90.

The interval in time between receiving the reflected ultrasonic wave 52 and receiving the reflected ultrasonic wave 54 defines a range when other ultrasonic wave components may also be received from reflections or refractions of the original ultrasonic wave 51 through the test subject 90. If the interior of test subject 90 in the propagation range of the ultrasonic waves from ultrasonic wave transducer 30 is smoothly continuous, then the major portion of the ultrasonic waves that refract through the forward surface 91 of the test subject 90 may be expected to propagate smoothly through test subject 90, reflect off the back surface of test subject 90, and return to be picked up again by ultrasonic wave transducer 30. In this expected case, ultrasonic wave transducer 30 may be expected to receive a first spike of incoming ultrasonic waves coinciding with reception of reflected ultrasonic wave 52, and later a second spike of incoming ultrasonic waves coinciding with reception of reflected ultrasonic wave 54, and little else (other than, for example, later, fainter echoes from minor components of the reflected ultrasonic wave 54 that reflect back inwardly from the forward surface 91, reflect again off of back surface 92, then refract out through forward surface 91 to finally be received by ultrasonic wave transducer 30).

On the other hand, any internal discontinuities hidden within test subject 90 will produce additional, unexpected influences on the ultrasonic waves propagating through test subject 90. For example, another component of ultrasonic wave 51 may encounter internal defect 93 hidden within test subject 90. This component of ultrasonic wave 51 may reflect off of and refract through irregular surfaces of internal defect 93 to be scattered in several directions, a portion of which may reflect back in the direction of ultrasonic wave transducer 30. This reflected portion may be referred to as defect detection wave component 53. The angles and irregularities of the internal defect 93 may produce a received ultrasonic wave signal with a distended shape and that extends over a longer duration of time than the sharp signals from the reflections from the smooth forward surface 91 and back surface 92 of the test subject 90. The timing of the received signal from the internal defect 93, intermediate to the expected signals from the forward surface 91 and back surface 92, provides a clear indication that there is a discontinuity in test subject 90 where continuity is expected if test subject 90 is properly formed.

Figure 2:
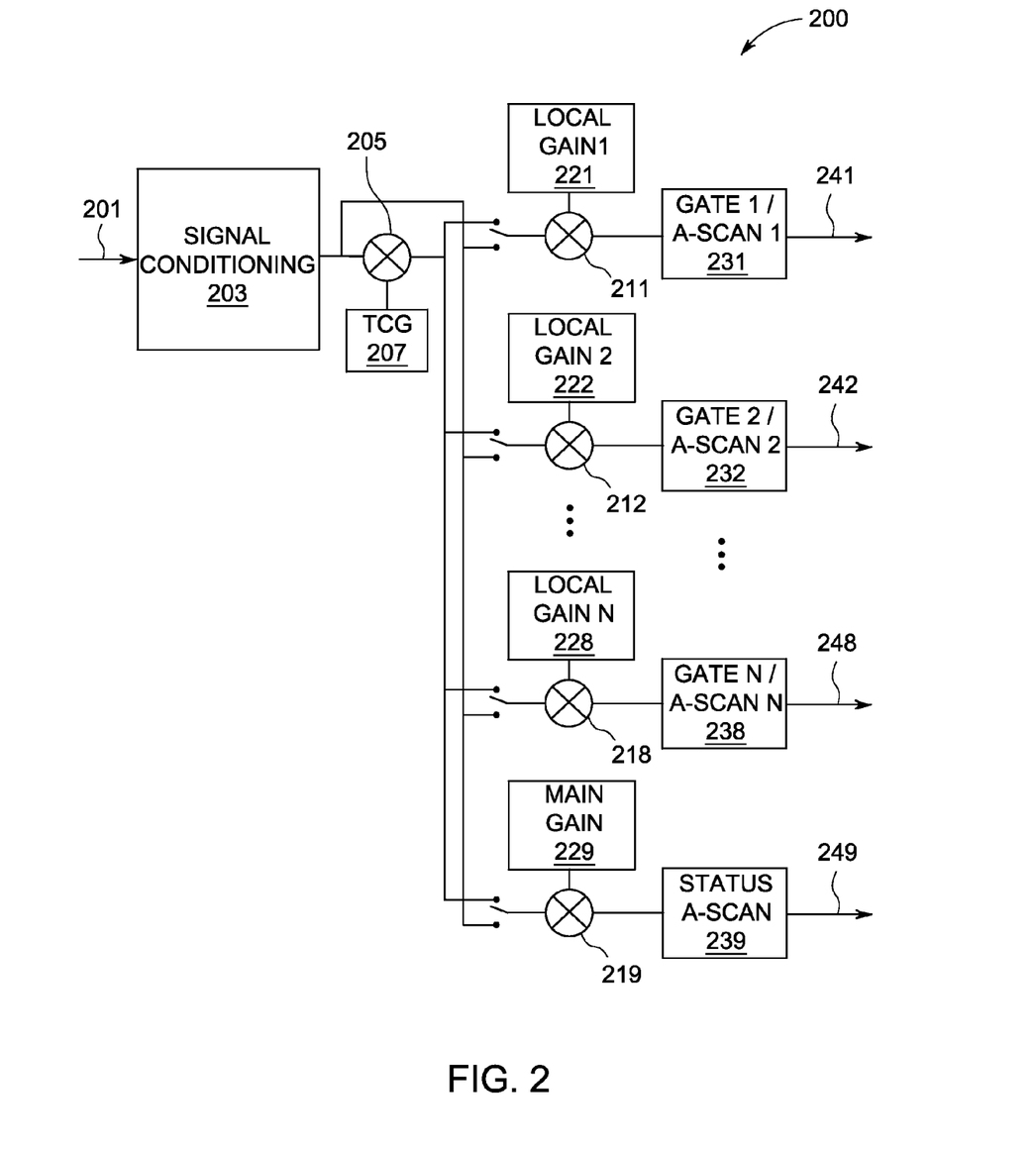
FIG. 2 depicts a schematic block diagram for a device for providing signal graphs showing ultrasonic signals with a main gain and/or local gains versus depth in a test subject, in accordance with an illustrative embodiment.
Figure 3:
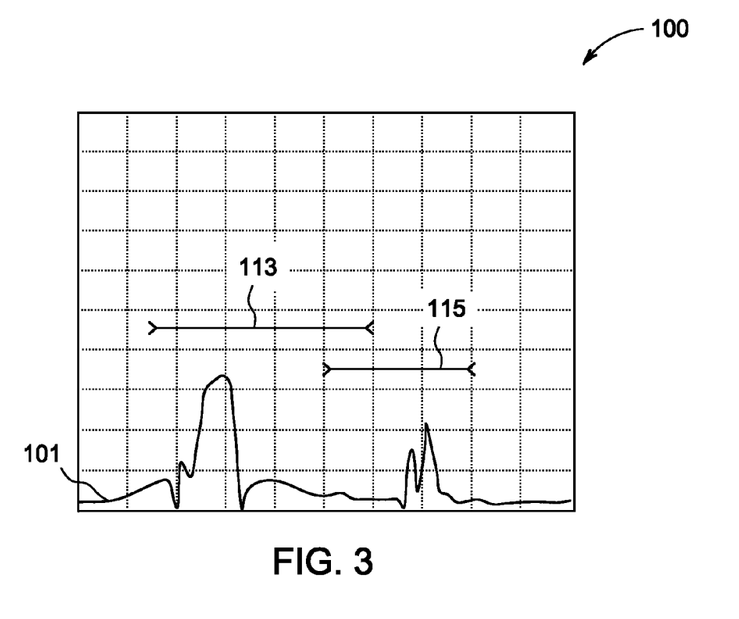
FIG. 3 depicts a signal graph showing an ultrasonic signal with a main gain versus depth in a test subject, in accordance with an illustrative embodiment.
Figure 4:
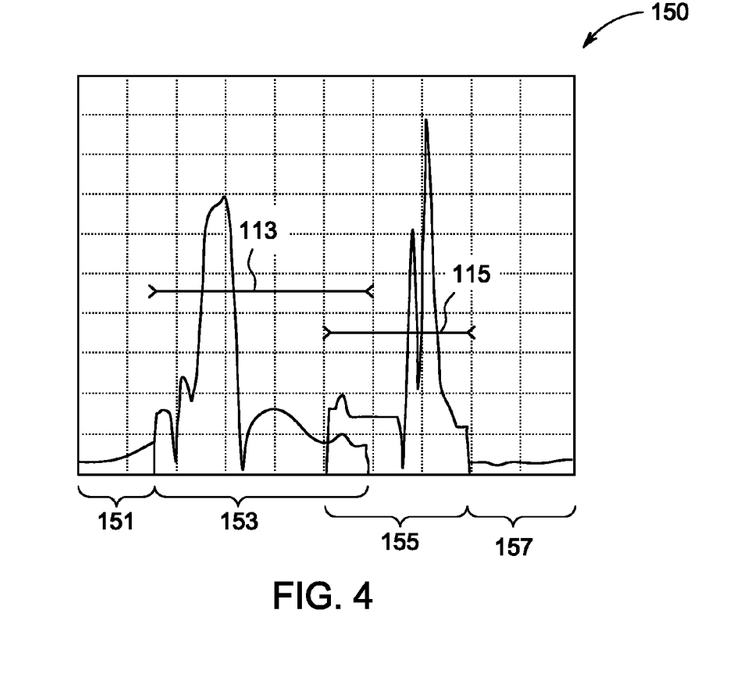
FIG. 4 depicts a signal graph showing ultrasonic signal segments with local gains versus depth in a test subject, in accordance with an illustrative embodiment.
Figure 5:
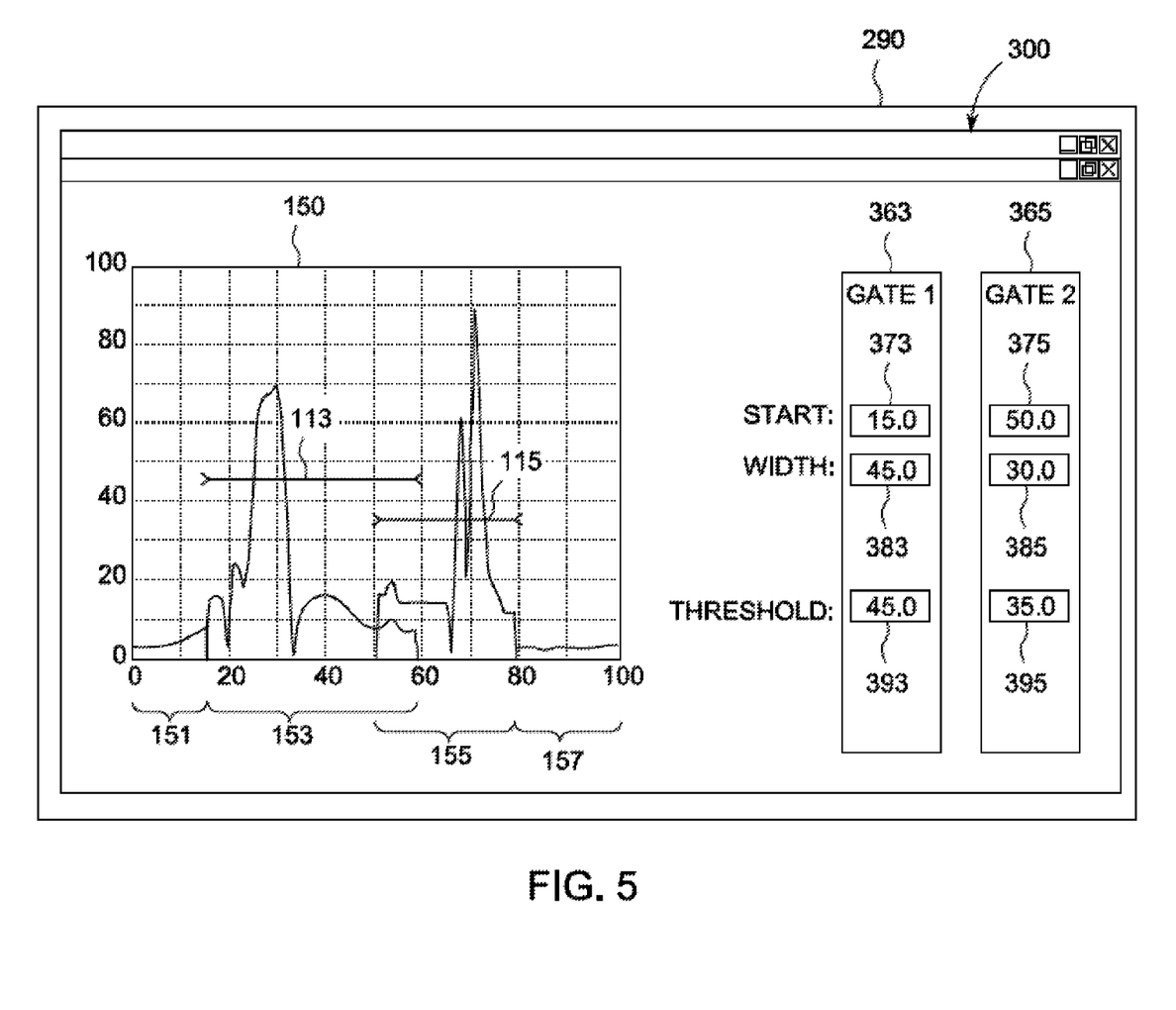
FIG. 5 depicts a simplified graphical user interface for a software program for controlling and displaying signal graphs showing ultrasonic signals with a main gain and/or local gains versus depth in a test subject, in accordance with an illustrative embodiment.

Illustrative examples of signal graphs showing ultrasonic signals received through ultrasonic wave transducer 30 are depicted in FIGS. 3-5 and described with reference thereto, below. FIG. 2 shows illustrative details for processing component 200, which may provide novel advantages in assisting with the detection of ultrasonic signals indicative of discontinuities such as internals defects in test subject 90.

FIG. 2 depicts a schematic block diagram for a processing component 200 which may provide signal graphs showing ultrasonic signals with a main gain and/or local gains versus depth in a test subject, in accordance with an illustrative embodiment. Processing component 200 may also include additional components beyond those depicted here, in various embodiments.

Processing component 200 includes an input line 201, which may have a communicative connection with ultrasonic wave transducer 30 through cable 31, and thereby be configured for receiving ultrasonic wave signals from ultrasonic wave transducer 30, for example. Input line 201 may connect first to signal conditioner 203. Signal conditioner 203 may therefore have a communicative connection with the receiver of the ultrasonic wave receiver 30. Signal conditioner 203 may include one or more amplifiers, one or more rectifiers, one or more filters, and/or other elements, for example. In various embodiments, signal conditioner 203 may be configured to perform at least one of amplifying, rectifying, and filtering an ultrasonic wave signal from the ultrasonic wave transducer 30, for example.

A gain multiplier 205 is connected to the output of signal conditioner 203. Gain multiplier 205 applies to time controlled gain component 207, which is described further below, after introducing the remaining elements of FIG. 2.

Processing component 200 further comprises a main gain component 229, with an associated gain multiplier 219, status A-scan element 239, and output 249. The main gain component 229 may have a communicative connection with the ultrasonic wave transducer 30, in this example through the signal conditioner 203. Any communicative connection may be through various other components that may form part of the communicative connection. The main gain component 229 may be configured for applying a main gain to an ultrasonic wave signal received via input line 201 from the ultrasonic wave receiver 30, for example. The gain applied may be in the form of an amplification of the voltage of the signal, as an illustrative example. Applying gain may involve any form of applying gain as understood by those skilled in the art. Main gain component 229 may thereby be configured for providing a main gain signal, which may illustratively represent a complete interval of the ultrasonic wave signal received via input line 201 from the ultrasonic wave receiver 30, with the main gain applied to the ultrasonic wave signal.

Processing component 200 also includes analogous gain element sets for each of a number of local gain options. In particular, as shown in this illustrative example, processing component 200 further includes: a first gain component 221, with an associated gain multiplier 211, status A-scan element 231, and output 241; a second gain component 222, with an associated gain multiplier 212, status A-scan element 232, and output 242; and, as schematically represented, up to an Nth gain component 228, with an associated gain multiplier 218, status A-scan element 238, and output 248, where N may be any number, and any number of gain components and associated elements may occur in various embodiments. Status A-scan elements 231, 232, and 238 may provide A-scan format output signals, for example. Processing component 200 may include a third gain component, a fourth gain component, or any number of additional gain components. In another embodiment, N may only be 2, and there may be only the main gain component 229, the first gain component 221, and the second gain component 222, as the only gain components in the processing component, for example. Processing component 200 may therefore provide a technical effect that involves providing a main gain and multiple local gains to an ultrasonic wave signal, for example.

The first gain component 221, the second gain component 222, and potentially up to the Nth gain component 228 may each have a communicative connection with the ultrasonic wave transducer 30, in this example through the signal conditioner 203. The first local gain component 221 may be configured for applying its own gain to a portion of the ultrasonic wave signal received via input line 201 from the ultrasonic wave receiver 30. This gain applied by first local gain component 221 to just a portion of the ultrasonic wave signal may be referred to as a first local gain. The portion of the ultrasonic wave signal to which the first local gain component 221 applies the first local gain may be defined as the portion of the ultrasonic wave signal that is within a signal gate, such as first signal gate 113 shown in FIGS. 3-5. The first signal gate 113 may be defined by a user and/or may be pre-selected in processing component 200, and is further explained with reference to FIGS. 3-5 below.

Similarly, the second local gain component 222 may be configured for applying its own gain to a different portion of the ultrasonic wave signal received via input line 201 from the ultrasonic wave receiver 30. This gain applied by second local gain component 221 to another portion of the ultrasonic wave signal may be referred to as a second local gain. The second local gain component 221 may apply the second local gain to a portion of the ultrasonic wave signal that is within a second signal gate 115 as shown in FIGS. 3-5 and further described below.

As is seen in FIG. 2, signal conditioner 203 has direct lines out to first gain component 221, second gain component 222, Nth gain component 228, and main gain component 229, and their associated elements, in particular to gain multipliers 211, 212, 218, and 219, while alternate lines lead to the same components from time controlled gain multiplier 205. In this way, time controlled gain, as controlled by time controlled gain component 207, may optionally be applied or not. The time controlled gain component 207 may be configured for providing a user-selectable option for varying the gain over time, including for the portion of the ultrasonic wave signal within the first signal gate 113 and the portion of the ultrasonic wave signal within the second signal gate 115. This may be used as an additional option or an additional tool for varying the gain over time, and therefore effectively over the range of depth within the test object 90.

Outputs 241, 242, 248, and 249, as shown in FIG. 2, may all be included in output component 23 as shown in FIG. 1, in an illustrative embodiment. Output component 23 may therefore output the ultrasonic wave signal with the main gain applied to it, the portion of the ultrasonic wave signal with the first local gain applied to it, and the portion of the ultrasonic wave signal with the second local gain applied to it, for example. Output component 23 may transmit this information to computing device 280, as seen in FIG. 1. Transmitting this information may be via a direct wireless or hard-line connection between processing component 200 and computing device 280, or by any intermediate communications infrastructure and/or elements thereof such as a wireless network, an Ethernet, a gateway, a router, and so forth. So, in this illustrative example, monitor 290 of computing device 280 may therefore have a communicative connection with the output component 23 of processing component 200, and thereby be configured to display signal graphs showing ultrasonic signals with a main gain and/or local gains versus depth in a test subject, for example.

While processing component 200 is depicted in terms of a particular illustrative circuitry hardware implementation in this illustrative embodiment, other embodiments may have the same or analogous functions implemented in software, in any of a variety of programming implementations, or any of several other hardware variations, or any combination of hardware and software, for example.

FIG. 3 depicts a signal graph 100 showing ultrasonic signal 101 with a main gain versus depth in a test subject, in accordance with an illustrative embodiment based on an A-scan format, as is familiar to those in the art, and aspects of which are also used in subsequent FIGS. 4 and 5. A first local signal gate 113 is depicted, as an interval that defines a first portion of the ultrasonic wave signal 101 as provided by processing component 200 based on readings from the ultrasonic wave receiver 30. The first local signal gate 113 defines a section of the ultrasonic wave signal 101 that coincides with a given portion of the test subject 90, from a selected beginning depth and extending therefrom across a selected range, as further described and depicted with reference to FIG. 5 below. Similarly, a second local signal gate 115 defines a second portion of the ultrasonic wave signal 101 based on the readings by the ultrasonic wave receiver 30, also with a selected beginning depth and extending therefrom across a selected range within the test subject. These two intermediate, local portions of the ultrasonic wave signal 101 therefore define intermediate depths within a test subject (not necessarily test subject 90 of FIG. 1) as candidate sections for examining for any potential defects, in an illustrative embodiment. First local signal gate 113 and second local signal gate 115 may be set with parameters that may be defined by a user and/or may be pre-selected in processing component 200, as is explained in more detail below with reference to FIG. 5. The first signal gate 113 and the second signal gate 115 may also overlap each other, as shown in FIGS. 3-5.

FIG. 4 depicts a signal graph 150 showing first local gain signal 153 and second local gain signal 155, amid main gain signal segments 151 and 157, in accordance with an illustrative embodiment. First local gain signal 153 is provided by applying the gain from first gain component 221 to a local portion of ultrasonic wave signal 101 defined by the first local signal gate 113, coinciding with a selected starting depth and width or range of depth within a test subject. Similarly, second local gain signal 155 is provided by applying the gain from second gain component 222 to a local portion of ultrasonic wave signal 101 defined by the first local signal gate 115, coinciding with a selected starting depth and width or range of depth within a test subject, though one that may overlap with the portion of the test subject covered by first local gain signal 153, in this illustrative embodiment. The overlap between the first local gain signal 153 and the second local gain signal 155 may help ensure that any defect at a depth proximate to the boundary between the ranges within the test subject covered by the two local gain signals is not overlooked, for example. Main gain signal segments 151 and 157 are segments of ultrasonic wave signal 101 with only the main gain from main gain component 229 applied to them, in this illustrative embodiment. Main gain signal segments 151 and 157, first local gain signal 153, and second local gain signal 155 may all be shown in signal graph 150 at the same time, in this illustrative embodiment.

First local gain signal 153 has had a first gain applied to it, which may modify its amplitude relative to the main gain level. For instance, first local gain signal 153 increases its amplitude beyond the main gain level shown in FIG. 3, in this illustrative example. A local gain signal may also detent or decrease rather than amplify or increase the signal in other embodiments. For example, this first gain applied to first local gain signal 153 may be applied by first gain component 221 as shown in FIG. 2, in this illustrative embodiment. Similarly, second local gain signal 155 has had a second gain applied to it, which may modify its amplitude relative to the main gain level. Second local gain signal 155 increases its amplitude beyond the main gain level shown in FIG. 3, in this illustrative example, and this second gain applied to first local gain signal 153 may be applied by second gain component 222 as shown in FIG. 2, in this illustrative embodiment. The first local gain component 221 is therefore configured for providing a first local gain signal 153 with a greater amplitude than the main output signal of ultrasonic signal 101, and the second local gain component 222 is analogously configured for providing the second local gain signal 155 with a greater amplitude than the main output signal of ultrasonic signal 101, in this illustrative example. Either the first or second local gains may modify the ultrasonic wave signal to either increase it or decrease it, in other examples. For example, in other embodiments, a signal gate may be set to cover a range of depth expected to include the forward surface 91 and another a signal gate may be set to cover a range of depth expected to include the back surface 92, and the signals from these surfaces may be relatively very strong, such that they would exceed the full height of a signal graph under the main gain. The local gains applied to these signal gates covering the forward surface 91 and the back surface 92 of the test subject 90 may be set to modify the ultrasonic wave signal by reducing the ultrasonic wave signal relative to the main gain, in this illustrative example. In this way, the peak of the signal within these two signal gates may be brought within the y-axis range of the signal graph 150 and enable a user to see and understand the shape of the complete signal, for example. As an illustrative context of use, ultrasonic scanning system 10 may also be useful for measuring the thickness of a test subject, in addition to or instead of evaluating the test subject 90 for abnormalities. In this illustrative context, carefully characterizing the forward surface 91 and the back surface 92 of the test subject 90 may be the primary goal for the use of ultrasonic scanning system 10.

The amplitudes of the original signal peaks shown in FIG. 3, covered by first local signal gate 113 and second local signal gate 115 respectively, are not particularly large. They may be representative of other signals that may be even less prominent yet that still actually are indicative of internal defects. There may be significant noise that may further reduce the relative prominence of the original signal peaks, and they may be difficult for a user making ultrasonic scans of a test subject to observe. The gain applied to these signals as shown in FIG. 4 makes these signal segments unmistakable, and thereby help ensure ultrasonic scan operators to be able to notice every actual sign of an internal defect detected by the ultrasonic scanning system 10. For example, processing component 200 may also be configured to apply the first local gain such that the first local gain signal 153 is displayed in signal graph 150 on the monitor 290 to occupy over half of a height of the signal graph 150, and to apply the second local gain such that the second local gain signal 155 is displayed in the signal graph 150 on the monitor 290 to occupy over half of the height of the signal graph 150. As a particular example, the parameters may be pre-selected to boost the first local gain signal 153 and the second local gain signal 155 up to a nominal relative amplitude of somewhere around approximately 80% of the full height of the signal graph 150, as an illustrative example. Further illustrative examples are discussed below with reference to FIG. 5.

Additionally, the original defect indicative signal peaks as seen in ultrasonic wave signal 101 in FIG. 3, covered by first local gain signal 153 and second local gain signal 155 as seen in FIG. 4, are unequal, with the later-appearing defect peak coinciding with second local signal gate 115 significantly smaller and weaker than the defect peak coinciding with first local signal gate 113. This may be due to the inherent nature of factors such as the diffusion of the ultrasonic signals over the course of propagation within the test subject 90, so that the farther away a defect is from the forward surface 91 and the farther toward the back surface 92, the fainter its signal appears under the uniform main gain as applied originally to the ultrasonic signal 101 as in FIG. 3.

Therefore, in some illustrative examples, this increasing faintness with depth can be compensated for by increasing the gain for deeper intervals. As seen in the illustrative embodiment of FIG. 4, the signal peak for ultrasonic signal segment 155, coincident with second local signal gate 115, is actually higher than the signal peak for ultrasonic signal segment 153 coincident with first local signal gate 113, even though the underlying signal was weaker. This is due to applying an even higher level of gain with the second gain component 222 than with the first gain component 221, and an even greater increase in gain over the default main gain applied to ultrasonic signal 101, in recognition of and compensation for the increasing faintness of internal defect signals with depth within the test subject. The second local gain component 222 may therefore be configured for providing the second local gain signal 155 with a greater amplitude than the first local gain signal 153, in this illustrative embodiment.

Similarly, the Nth local gain component 228 in FIG. 2 may represent a third local gain component or a fourth or greater local gain component, also with a communicative connection with the ultrasonic wave receiver. In the case of a third local gain component, for example, the third local gain component may be configured for providing a third local gain signal representing a third portion of the ultrasonic wave signal 101 based on the readings of the ultrasonic wave receiver. This third local gain component may apply a third local gain to a third portion of the ultrasonic wave signal such that it is different than either the first portion of the ultrasonic wave signal or the second portion of the ultrasonic wave signal. In the case of a fourth or higher local gain component, each of the additional local gain components may illustratively be configured for applying an additional local gain to an additional portion of the ultrasonic wave signal received by the ultrasonic wave receiver to provide a fourth local gain signal, wherein, for example, the fourth local gain signal is different than either the first local gain signal, the second local gain signal, or the third local gain signal. The third local gain component may be configured for providing the third local gain signal with a greater or lower amplitude than the second local gain signal, and the fourth local gain component may be configured for providing the fourth local gain signal with a greater or lower amplitude than the third local gain signal, and any of the local gain components may be configured for modifying their local gain signals to be either greater than or lower than the main gain, in various illustrative examples.

Another element that may be used to clarify different local gain signals, with a different local gain applied to each one, is to use a different color for each local gain signal. While not shown in the black-and-white depiction of FIG. 4, each of first local gain signal 153 and second local gain signal 155 may be depicted in the signal graph 150 on the monitor 290 in a different color from each other and from the signal segments subject only to the main gain, e.g. ultrasonic signal segments 151 and 157. The device may be configured for displaying the main gain signal in a first color on the monitor 290, the first local gain signal 153 in a second color on the monitor 290, and the second local gain signal 155 in a third color on the monitor 290.

The signal gates may also be shown in different colors, and with colors that match their corresponding local gain signals. So, for example, first signal gate 113 and first local gain signal 153 may both be depicted in a single first color, such as blue, while second signal gate 115 and second local gain signal 155 may both be depicted in a single second color, such as yellow, while main gain signal segments 151 and 157 may be depicted in yet another color, such as green, for example. This type of color contrast may further facilitate an operator's understanding of which local gain signals are subject to which local gain, and where the individual local gain signals are separate from each other and/or overlap each other, in this illustrative embodiment.

FIG. 5 depicts a simplified graphical user interface 300 for a software program for controlling and displaying signal graphs showing ultrasonic RF signals with a main gain and/or local gains versus depth in a test subject, in accordance with an illustrative embodiment. Graphical user interface 300 is shown being displayed on monitor 290, such as is included in computing device 280 as shown in FIG. 1. Monitor 290 may have a communicative connection, via relevant intermediary elements, with output component 23 of ultrasonic control device 20, and thereby to the main gain component 229, the first local gain component 221, the second local gain component 222, and other local gain components of processing component 200. This may help enable monitor 290 to be configured for displaying signal graph 150 as in FIG. 4, including first local gain signal 153, second local gain signal 155, and main gain signal segments 151 and 157. Signal graph 150 is also depicted with reference numerals along both the x-axis and the y-axis, where the x-axis numbers may indicate equivalent depth into a test subject based on propagation time of the ultrasonic wave through the test subject, and the y-axis numbers may indicate relative percentage of the height of the signal graph 150, for example.

Graphical user interface 300 includes a number of elements, including illustrative signal graph 150, and user control boxes 363 and 365. Signal graph 150 shows first local gain signal 153, second local gain signal 155, and main gain signal segments 151 and 157, indicating gain-boosted signal reflections versus depth in test subject 90, in accordance with an illustrative embodiment. Either of the first local gain signal 153 and the second local gain signal 155 may correspond to an internal defect or abnormality such as internal defect 93 as shown in FIG. 1, in an illustrative embodiment. (The other local gain signal may correspond to a different internal defect (not depicted in FIG. 1) or a different portion of internal defect 93, for example.) Local signal gates 113 and 115 are depicted across ranges corresponding to different segments of the depth of the test subject, with overlaps among them.

FIG. 5 further demonstrates an illustrative example of the range of relative amplitude or height within the signal graph 150 occupied by the local gain signals. In this illustrative embodiment, comparing the first local gain signal 153 and the second local gain signal 155 to the percentage reference numbers up the y-axis of the signal graph 150 within the graphical user interface 300 displayed on monitor 290 as depicted in FIG. 5, it is seen that first local gain signal 153 extends upward to an apparent amplitude of approximately 68% of the height of the signal graph 150, while the second local gain signal 155 extends upward to an apparent amplitude of approximately 88% of the height of the signal graph 150. The locally applied gains applied for these local gain signals therefore make detections of internal defects in the test subject very hard to escape a scanning operator's notice, in this illustrative embodiment.

Each of user control boxes 363 and 365 provides selectable options to determine the parameters of one of local signal gates 113 and 115, with user control box 363 providing parameters for local signal gate 113, and user control box 365 providing parameters for local signal gate 115, in this illustrative embodiment. In particular, each of the user control boxes 363 and 365 provides options for controlling the parameters of a start position of the corresponding local signal gate, a width of the local signal gate, and a threshold for the local signal gate. For example, user control box 363 provides start field 373 for selecting a start position for local signal gate 113, in terms of the depth into the test subject 90, corresponding to position along the x-axis in signal graph 150. User control box 363 also provides width field 383 for selecting a width from the start position for local signal gate 113, in terms of the further range of depth into the test subject 90 from the start position. User control box 363 also provides threshold field 393 for selecting a signal threshold for local signal gate 113, corresponding to the signal amplitude or the y-axis in signal graph 150. The threshold for a given local signal gate may be pre-selected or may be selected by a user as a standard against which to evaluate the height of the local gain signal and how significant of an abnormality or defect the local gain signal may indicate, relative to, noise or other spurious signals, or possible reflections off of potential tiny defects that are below the level of interest being tested for. The threshold may be set to a value which the signal portion in that local signal gate should only reach if it is significant enough to meaningfully indicate an internal defect, abnormality, or other discontinuity of sufficient interest within the test subject, in an illustrative embodiment. The threshold may be selected at 20%, 30%, 40%, or any other percentage of the y-axis range of the signal graph 150 within the given parameters of the implementation, and may be selected depending on any particular context of testing, and any desired level of tolerance for internal abnormalities. As one illustrative example, an initial calibration may be performed with a calibration test subject having a well-characterized test flaw at a known depth within it, to test the response of the ultrasonic wave signal to the well-characterized test flaw, and the threshold may be selected based on the response of the local gain to the ultrasonic wave signal to the calibration test flaw.

Analogously, user control box 365 includes start field 375, width field 385, and threshold field 395, to control these parameters for local signal gates 115, in this illustrative embodiment. Other user control boxes may also be included to control parameters for other local signal gates or for the signal gates covering the signal portions from the forward surface 91 and the back surface 92 of the test subject 90, for example. Any of a wide variety of other DOM elements or GUI elements may also be included in different implementations of graphical user interface 300, in various embodiments. In various embodiments, an automated gate tracking system may also be set up to compare local gain signals with the thresholds associated with their signal gates. In this type of embodiment, processing component 200 or some other component of ultrasonic scanning system 10 may include an automated gate tracking system that compares a local gain signal for a signal gate with the threshold associated with that signal gate, and provide an indication if the local gain signal for that signal gate is greater than or equal to the threshold for that signal gate, for example. This may be performed without a human operator evaluating a signal graph, or without a signal graph being displayed on a monitor, for example. Additionally, in some embodiments, an automated gate tracking system may be set up to dynamically change the starting point and the width of the signal gates. For example, an automated gate tracking system may be configured to alter at least one of a starting depth of a first signal gate or a width of the first signal gate to be applied to a subsequent ultrasonic wave signal based on the first local gain signal. The automated gate tracking system may therefore dynamically alter the starting point and the width of the signal gates in response to the local gain signals of prior test runs, such as if the peak of the first local gain signal is on or near an edge of the first signal gate, for example.

Various methods are therefore disclosed, in different illustrative embodiments, for using an ultrasonic signal to examine a test subject and displaying information gained using the ultrasonic signal. In some embodiments, a method may include transmitting an ultrasonic signal through a test subject; receiving an incoming ultrasonic signal that has passed through the test subject; applying a main gain to the incoming ultrasonic signal; applying a first local gain to a first portion of the incoming ultrasonic signal corresponding to a first portion of the test subject; applying a second local gain to a second portion of the incoming ultrasonic signal corresponding to a second portion of the test subject; and displaying, on a monitor, a main gain signal representing the incoming ultrasonic signal with the main gain applied thereto, a first local gain signal representing the first portion of the incoming ultrasonic signal with the first local gain applied thereto, and a second local gain signal representing the second portion of the incoming ultrasonic signal with the second local gain applied thereto.

A method may further include displaying the main gain signal in a first color, displaying the first local gain signal in a second color, and displaying the second local gain signal in a third color, in an illustrative embodiment.

Various devices, systems, and methods as disclosed herein therefore provide novel ways to ensure that operators of ultrasonic scanning equipment will detect relevant defects or other discontinuities of interest in test subjects, among a variety of other advantages, in accordance with a range of varying embodiments.

While processing component 200 is depicted in FIG. 2 as including certain particular circuit elements, a processing component in various other embodiments may be implemented in any of a variety of forms such as a central processing unit (CPU), a field programmable gate array (FPGA), a programmable logic device (PLD) or a complex programmable logic device (CPLD), an application-specific integrated circuit (ASIC), or any other type of processing unit or chip, in different implementations, and may still perform the same or analogous functions as those described herein.

A software program for controlling and displaying signal graphs showing ultrasonic RF signals with a main gain and/or local gains versus depth in a test subject may be programmed using any of a wide variety of languages, such as C, C++, Java, C#, Perl, PHP, Scala, Python, Ruby, Smalltalk, Haskell, Common Lisp, or Clojure, for example. Any of a variety of frameworks may be used to facilitate such programming. A software program for controlling and displaying signal graphs showing ultrasonic RF signals with a main gain and/or local gains versus depth in a test subject may also use any of a wide variety of database architecture, database management system, and database query language. For example, it may use any variation of a SQL database query language, such as those conforming to the ISO/IEC 9075 standard. The software program may be implemented in the form of a desktop application, a mobile application, a web application, or any other form of application. For a browser-based application, the design of the interface may include the use of HTML, HTML5, CSS, CSS3, JavaScript, AJAX, and/or any other scripting or design tool or language, in various embodiments.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A device comprising:
   an input line;
   a main gain component, having a communicative connection with the input line, the main gain component configured for applying a main gain to an ultrasonic wave signal received via the input line, thereby providing a main gain signal;
   a first local gain component, having a communicative connection with the input line, the first local gain component configured for applying a first local gain to a first portion of the ultrasonic wave signal within a first signal gate, and thereby providing a first local gain signal; and
   a second local gain component, having a communicative connection with the input line, the second local gain component configured for applying a second local gain to a second portion of the ultrasonic wave signal within a second signal gate, and thereby providing a second local gain signal.

2. The device of claim 1, wherein the first local gain component is configured for applying the first local gain with a modified amplitude relative to the main gain, thereby providing the first local gain signal with a modified amplitude relative to the main gain signal, and wherein the second local gain component is configured for applying the second local gain with a modified amplitude relative to the main gain, thereby providing the second local gain signal with a modified amplitude relative to the main gain signal.

3. The device of claim 2, wherein the second local gain component is configured for providing the second local gain with a modified amplitude relative to the first local gain.

4. The device of claim 3, further comprising one or more additional local gain components comprising at least a third local gain component, having a communicative connection with the input line, wherein each of the additional local gain components is configured for applying an additional local gain to an additional portion of the ultrasonic wave signal within an additional signal gate, and thereby providing an additional local gain signal.

5. The device of claim 4, wherein the third local gain component is configured for providing the third local gain with a modified amplitude relative to the first local gain or the second local gain.

6. The device of claim 1, wherein the first signal gate and the second signal gate overlap each other.

7. The device of claim 1, further comprising a signal conditioner having a communicative connection with the input line, wherein the communicative connections of the main gain component, the first local gain component, and the second local gain component with the input line are through the signal conditioner.

8. The device of claim 7, wherein the signal conditioner is configured to perform at least one of amplifying, rectifying, and filtering the ultrasonic wave signal from the input line, before the ultrasonic wave signal is received by the main gain component, the first local gain component, or second local gain component.

9. The device of claim 1, further comprising an ultrasonic wave receiver, having a communicative connection with the input line and configured to provide the ultrasonic wave signal.

10. The device of claim 9, wherein the ultrasonic wave receiver is comprised in an ultrasonic wave transducer that further serves as an ultrasonic wave transmitter, configured for transmitting a source ultrasonic wave such that the ultrasonic wave receiver is configured to receive reflections of the source ultrasonic wave.

11. The device of claim 1, further comprising a monitor with a communicative connection with the main gain component, the first local gain component, and the second local gain component, such that the monitor is configured for displaying the main gain signal in a first color, the first local gain signal in a second color, and the second local gain signal in a third color on the monitor.

12. The device of claim 1, further comprising a time controlled gain component, having a communicative connection with the main gain component, the first local gain component, and the second local gain component, wherein the time controlled gain component is configured for providing a user-selectable option for varying gain over time for the first local gain signal and the second local gain signal.

13. An ultrasonic scanning system comprising:
an ultrasonic wave transducer configured for transmitting and receiving ultrasonic waves, and generating an ultrasonic wave signal based on ultrasonic waves it receives;
a processing component having a communicative connection with the ultrasonic wave receiver and configured to receive the ultrasonic wave signal and to apply a main gain to the ultrasonic wave signal to provide a main gain signal, to apply a first local gain to a first portion of the ultrasonic wave signal within a first signal gate to provide a first local gain signal, and to apply a second local gain to a second portion of the ultrasonic wave signal within a second signal gate to provide a second local gain signal; and
an output component for outputting the main gain signal, the first local gain signal, and the second local gain signal.

14. The ultrasonic scanning system of claim 13, further comprising a user interface enabling a user to select at least one of a starting depth of the first signal gate, a width of the first signal gate, and a threshold amplitude of the first signal gate.

15. The ultrasonic scanning system of claim 14, wherein the ultrasonic scanning system is configured to indicate whether a portion of the ultrasonic wave signal meets the threshold amplitude of the first signal gate within a range of depth defined by the starting depth of the first signal gate and the width of the first signal gate.

16. The ultrasonic scanning system of claim 13, wherein the first signal gate and the second signal gate overlap each other.

17. The ultrasonic scanning system of claim 13, further comprising a monitor having a communicative connection with the output component, wherein the monitor is configured to display the main gain signal in a first color, the first local gain signal in a second color, and the second local gain signal in a third color on the monitor.

18. The ultrasonic scanning system of claim 13, further comprising an automated gate tracking system that compares the first local gain signal with a first threshold associated with the first signal gate, and provides an indication if the first local gain signal is greater than or equal to the first threshold.

19. The ultrasonic scanning system of claim 13, further comprising an automated gate tracking system that is configured to alter at least one of a starting depth of the first signal gate or a width of the first signal gate to be applied to a subsequent ultrasonic wave signal based on the first local gain signal.

20. A method for scanning a test subject with an ultrasonic wave, the method comprising:
transmitting the ultrasonic wave through the test subject;
receiving a reflected ultrasonic wave from the test subject;
generating an ultrasonic signal based on the reflected ultrasonic wave;
applying a main gain to the ultrasonic signal;
applying a first local gain to a first portion of the ultrasonic signal corresponding to a first portion of the test subject;
applying a second local gain to a second portion of the ultrasonic signal corresponding to a second portion of the test subject; and
displaying on a monitor a graph of the ultrasonic signal with the main gain applied to the ultrasonic signal, the first portion of the ultrasonic signal with the first local gain applied to the first portion of the ultrasonic signal, and the second portion of the ultrasonic signal with the first local gain applied to the second portion of the ultrasonic signal.

* * * * *